United States Patent [19]

Schwark et al.

[11] Patent Number: 5,567,734
[45] Date of Patent: Oct. 22, 1996

[54] PHENYL-SUBSTITUTED ALKYLCARBOGUANIDIDES CARRYING PERFLUOROALKYL GROUPS, A PROCESS FOR THEIR PREPARATION, THEIR USE AS A MEDICAMENT OR A DIAGNOSTIC AGENT, AND A MEDICAMENT CONTAINING THEM

[75] Inventors: Jan-Robert Schwark, Frankfurt; Heinz-Werner Kleemann, Bad Homburg; Hans-Jochen Lang, Hofheim; Andreas Weichert, Egelsbach; Wolfgang Scholz, Eschborn; Udo Albus, Florstadt, all of Germany

[73] Assignee: Hoechst Aktiengesellschaft, Frankfurt am Main, Germany

[21] Appl. No.: 377,012

[22] Filed: Jan. 23, 1995

[30] Foreign Application Priority Data

Jan. 25, 1994 [DE] Germany ............... 44 02 057.0
Apr. 19, 1994 [DE] Germany ............... 44 13 615.3

[51] Int. Cl.⁶ .................... A61K 31/165; C07C 233/34
[52] U.S. Cl. .................... 514/617; 514/619; 514/620; 514/622; 514/522; 558/414; 564/147; 564/161; 564/163; 564/164; 564/165
[58] Field of Search .................... 564/147, 161, 564/163, 164, 165; 514/614, 615, 617, 619, 620, 622; 558/414

[56] References Cited

U.S. PATENT DOCUMENTS 3,780,027 12/1973 Cragoe et al. ................ 549/494
5,091,394 2/1992 Englert et al. ................ 514/331

FOREIGN PATENT DOCUMENTS

0087218A1 8/1983 European Pat. Off. .
556672A1 8/1993 European Pat. Off. .
0627413A1 12/1994 European Pat. Off. .
2055093 2/1981 United Kingdom .
WOA84/00875 3/1984 WIPO .
8400875 3/1984 WIPO .

OTHER PUBLICATIONS

Scholtysik et al., Arzn. Forsch., 39(1), Nr. 4, 1989 450–454.

Primary Examiner—Shailendra Kumar
Attorney, Agent, or Firm—Finnegan, Henderson, Farabow, Garrett & Dunner, L.L.P.

[57] ABSTRACT

Phenyl-substituted alkylcarboguanidides carrying perfluoroalkyl groups, of the formula I

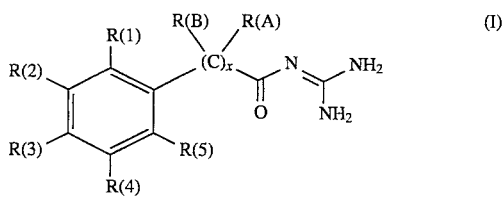

are described where R(A) and R(B) are H, Hal, CN, OR(6), alkyl, $O_r$-perfluoroalkyl or NR(7)R(8); R(6) is hydrogen, (cyclo)alk(en)yl, perfluoroalkyl, phenyl or benzyl; R(7) and R(8) are defined as R(6); X is 1–3; R(1) is H, alkyl or $—O_{0-1}(CH_2)O_{0-1}$ perfluoroalkyl; R(2), R(3), R(4) and R(5) are defined as R(1), with the condition, however, that R(1), R(2), R(3), R(4) and R(5) are not simultaneously hydrogen and that R(1), R(2), R(3), R(4) and R(5) can only be alkyl when at least one of the substituents R(A) or R(B) contains a $O_r(CH_2)_aC_bF_{2b+1}$ group; as are the pharmaceutically acceptable salts thereof. Methods of preparation of compounds of formula I are also described.

3 Claims, No Drawings

PHENYL-SUBSTITUTED ALKYLCARBOGUANIDIDES CARRYING PERFLUOROALKYL GROUPS, A PROCESS FOR THEIR PREPARATION, THEIR USE AS A MEDICAMENT OR A DIAGNOSTIC AGENT, AND A MEDICAMENT CONTAINING THEM

DESCRIPTION

The invention relates to phenyl-substituted alkylcarboguanidides, carrying perfluoroalkyl groups, of the formula I

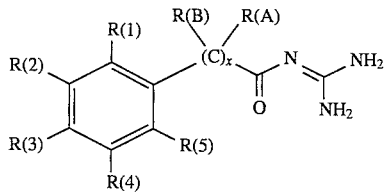

in which:

R(A) is hydrogen, F, Cl, Br, I, CN, OR(6), $(C_1-C_8)$-alkyl, $(C_3-C_8)$-cycloalkyl, $O_r(CH_2)_aC_bF_{2b+1}$ or NR(7)R(8), r is zero or 1, a is zero, 1, 2, 3 or 4, b is 1, 2, 3, 4, 5, 6, 7 or 8;

R(6) is hydrogen, $(C_1-C_8)$-alkyl, $(C_3-C_8)$-alkenyl, $(C_3-C_8)$-cycloalkyl, phenyl or benzyl, where the aromatic radicals are unsubstituted or substituted by 1–3 substituents selected from the group consisting of F, Cl, $CF_3$, methyl, methoxy and NR(9)R(10), R(9) and R(10) are H, $(C_1-C_4)$-alkyl or $(C_1-C_4)$-perfluoroalkyl;

R(7) and R(8) are, independently of each other, defined as R(6);

R(B) is, independently, defined as R(A);

X is 1, 2 or 3;

R(1) is hydrogen, $(C_1-C_8)$-alkyl, $(C_3-C_8)$-cycloalkyl, $-O_t(CH_2)_dC_eF_{2e+1}$, F, Cl, Br, I or CN, t is zero or 1, d is zero, 1, 2, 3 or 4, e is 1, 2, 3, 4, 5, 6, 7 or 8;

R(2), R(3), R(4) and R(5) are, independently of each other, defined as R(1), with the condition, however, that at least one of the substituents R(1), R(2), R(3), R(4), R(5), R(A) and R(B) is a $-O_t(CH_2)_dC_eF_{2e+1}$ or a $O_r(CH_2)_aC_bF_2+1$ group, and the pharmaceutically tolerated salts thereof.

Compounds of the formula I are preferred in which:

R(A) is hydrogen, F, Cl, Br, I, CN, OR(6), $(C_1-C_8)$-alkyl, $-C_bF_2+1$ or NR(7)R(8), b is 1, 2, 3 or 4;

R(6) is hydrogen, $(C_1-C_4)$-alkyl, $(C_3-C_8)$-alkenyl, $(C_3-C_8)$-cycloalkyl, phenyl or benzyl, where the aromatic radicals are unsubstituted or substituted by 1–3 substituents selected from the group consisting of F, Cl, $CF_3$, methyl, methoxy and NR(9)R(10), R(9) and R(10) are H, $CH_3$ or $CF_3$;

R(7) and R(8) are, independently of each other, defined as R(6);

R(B) is, independently, defined as R(A),

X is 1, 2 or 3;

R(1) is hydrogen, $(C_1-C_8)$-alkyl, $-C_eF_{2e+1}$, F, Cl, Br, I or CN;

e is 1, 2, 3, 4, 5, 6, 7 or 8;

R(2), R(3), R(4) and R(5) are, independently of each other, defined as R(1), with the condition, however, that at least one of the substituents R(1), R(2), R(3), R(4), R(5), R(A) and R(B) is a $C_eF_{2e+1}$ or a $C_bF_2+1$, and the pharmaceutically tolerated salts thereof.

Compounds of the formula I are particularly preferred in which:

R(A) is hydrogen, F, Cl, Br, I, CN, OR(6), $(C_1-C_8)$-alkyl, $-C_bF_2+1$ or NR(7)R(8);

b is 1, 2, 3 or 4;

R(6) is hydrogen, $(C_1-C_4)$-alkyl, $(C_1-C_4)$-perfluoroalkyl, phenyl, or benzyl, where the aromatic radicals are unsubstituted or substituted by 1–3 substituents selected from the group consisting of F, Cl, $CF_3$, methyl, methoxy and NR(9)R(10), R(9) and R(10) are H, $CH_3$ or $CF_3$;

R(7) and R(8) are, independently of each other, defined as R(6);

R(B) is, independently, defined as R(A),

X is 2,

R(1) is hydrogen, $(C_1-C_4)$-alkyl, $-C_eF_{2e+1}$, F or Cl;

e is 1, 2, 3 or 4;

R(2), R(3), R(4) and R(5) are, independently of each other, defined as R(1), with the condition, however, that at least one of the substituents R(1), R(2), R(3), R(4), R(5), R(A) and R(B) is a $C_eF_{2e+1}$ or a $C_bF_{2b+1}$, and the pharmaceutically tolerated salts thereof.

If the compound of the formula I contains one of more centers of asymmetry, these can be in either the S or the R configuration. The compounds may be present as optical isomers, as diastereomers, as racemates or as mixtures thereof.

The designated alkyl and perfluoroalkyl radicals may be either straight-chain or branched.

The invention additionally relates to a process for preparing the compound I, wherein compounds of the formula II

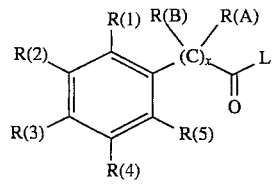

in which R(1) to R(5) and R(A) and also R(B) have the given meaning and L is a leaving group which can readily be substituted nucleophilically, are reacted with guanidine.

The activated acid derivatives of the formula II, in which L is an alkoxy, preferably a methoxy, group, a phenoxy group, phenylthio, a methylthio group, a 2-pyridylthio group or a nitrogen heterocycle, preferably 1-imidazolyl, are advantageously obtained, in a manner known per se, from the underlying carbonyl chlorides (formula II, L=Cl) which, for their part, can in turn be prepared, in a manner known per se, from the underlying carboxylic acids (formula II, L=OH), for example using thionyl chloride.

In addition to the carbonyl chlorides of the formula II (L=Cl), other activated acid derivatives of the formula II can also be prepared, in a manner known per se, directly from the underlying carboxylic acid derivatives (formula II, L=OH), as can, for example, the methyl esters of the formula II with L=$OCH_3$ by treatment with gaseous HCl in methanol, the imidazolides of the formula II by treatment with carbonyldiimidazole [L=1-imidazolyl, Staab, Angew. Chem. Int. Ed. Engl. 1, 351 to 367 (1962)], the mixed anhydrides II using Cl-COOC$_2$H$_5$ or tosyl chloride in the presence of triethylamine in an inert solvent, and also the activated carboxylic acids resulting from the use of dicyclohexylcarbodiimide (DCC) or O-[(cyano(ethoxycarbonyl)methylene)amino]-1,1,3,3-tetramethyluronium tetrafluoroborate ("TOTU") [Proceedings of the 21. European Peptide Symposium, Peptides 1990, Editors E. Giralt and D. Andreu, Escom, Leiden, 1991]. A series of suitable methods for preparing activated carboxylic acid derivatives of the formula II is given, with citation of the source literature, in J. March, Advanced Organic Chemistry, Third Edition (John Wiley & Sons, 1985), p. 350.

The reaction of an activated carboxylic acid derivative of the formula II with guanidine is effected, in a manner known per se, in a protic or aprotic, polar but inert, organic solvent. In this context, methanol, isopropanol or THF, at a temperature of from 20° C. up to the boiling temperature of these solvents, have proved to be of value when reacting the methyl carboxylates (II, L=OMe) with guanidine. Most of the reactions of compounds II with salt-free guanidine were advantageously carried out in aprotic, inert solvents such as THF, dimethoxyethane or dioxane. However, water can also be used as a solvent when reacting II with guanidine while making use of a base such as, for example, NaOH.

When L is Cl, the reaction is advantageously carried out in the presence of an acid capturing agent, for example in the form of excess guanidine, in order to bind the hydrohalic acid.

Some of the underlying carboxylic acid derivatives of the formula II are known and are described in the literature. The unknown compounds of the formula II can be prepared by methods which are known from the literature. The resulting carboxylic acids are converted into compounds I according to the invention by one of the above described process variants.

Introduction of some of the substituents is achieved using methods, known from the literature, of palladium-mediated cross coupling of aryl halides or aryl triflates with, for example, organostannanes, organoboronic acids, organoboranes, organocopper compounds, organozinc compounds or terminal alkynes.

In general, acylguanidines I are weak bases and can bind acid with the formation of salts. Salts of all pharmacologically tolerated acids, for example halides, in particular hydrochlorides, lactates, sulfates, citrates, tartrates, acetates, phosphates, methylsulfonates and p-toluenesulfonates, are suitable as acid addition salts.

The compounds I are substituted acylguanidines. The most prominent representative of the acylguanidines is the pyrazine derivative amiloride, which is used in therapy as a potassium-saving diuretic agent. Many other compounds of the amiloride type are described in the literature, such as, for example, dimethyl amiloride or ethylisopropyl amiloride.

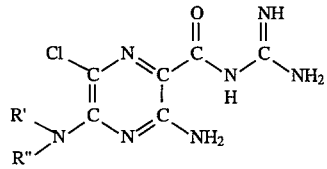

Amiloride: R' and R''=H
Dimethyl amiloride: R' and R''=CH$_3$
Ethylisopropyl amiloride: R'=C$_2$H$_5$ and R''=CH(CH$_3$)$_2$ In addition to this, investigations have been published which indicate that amiloride possesses antiarrhythmic properties (Circulation 79, 1257–63 (1989). However, the fact that this effect is only weakly expressed and is accompanied by hypotensive and saluretic effects, which are undesirable side effects when treating disturbances of cardiac rhythm, represents an obstacle to any widespread use of amiloride as an antiarrhythmic agent.

Indications that amiloride possesses antiarrhythmic properties were also obtained in experiments on isolated animal hearts (Eur. Heart J. 9 (suppl 1):167 (1988) (book of abstracts)). Thus, it was found on rat hearts, for example, that it was possible to use amiloride to completely suppress an artificially induced ventricular fibrillation. In this model, the abovementioned amiloride derivative ethylisopropyl amiloride was even more potent than amiloride.

U.S. Pat. No. 5,091,394 (HOE 89/F 288), EP-A-566 674 (HOE 92 /F 034) and U.S. Pat. No. 3,780,027 describe benzoylguanidines. The compounds according to the invention differ from those disclosed in these publications as a result of the —CR(A)R(B) group between the CO group and the phenyl radical.

WO 84/00875 discloses, inter alia, similar acylguanidines which, however, do not in any instance carry perfluoroalkyl groups.

Since all antiarrhythmically active guanidines are to date derived from arylcarboxylic or heteroarylcarboxylic acids, it was surprising, therefore, that, while the compounds according to the invention do not exhibit any undesirable and disadvantageous salidiuretic properties, they do exhibit very good antiarrhythmic properties as expressed, for example, in association with symptoms of oxygen lack. As a consequence of their pharmacological properties, the compounds are outstandingly suitable for use as antiarrhythmic pharmaceuticals with a cardioprotective component for the prophylaxis and treatment of infarction and for the treatment of angina pectoris, while also inhibiting or strongly reducing, in a preventive manner, the pathophysiological processes associated with the genesis of ischemically induced damage, in particular associated with the elicitation of ischemically induced cardiac arrhythmias. Due to their effect in protecting against pathological hypoxic and ischemic situations, the compounds of the formula I according to the invention can be used, as a consequence of inhibiting the cellular Na$^+$/H$^+$ exchange mechanism, as pharmaceuticals for treating all acute or chronic damage elicited by ischemia, or disorders which are primarily or secondarily induced thereby. This concerns their use as pharmaceuticals for surgical interventions, for example in organ transplantations, where the compounds can be used both for protecting the organs in the donor before and during removal, for protecting organs which have been removed, for example when treating them with or storing them in physiological bathing fluids, and when transferring them into the recipient organism. The compounds are also valuable pharmaceuticals, having a protective effect, for use when carrying out angioplastic surgery, for example on the heart or on peripheral vessels. In conformity with their protective effect against ischemically induced damage, the compounds are also suitable for use as pharmaceuticals for treating ischemias of the nervous system, in particular of the central nervous system, where they are suitable, for example, for treating stroke or cerebral edema. In addition to this, the compounds of the formula I according to the invention are also suitable for treating forms of shock, such as, for example, allergic, cardiogenic, hypovolemic and bacterial shock.

In addition to this, the compounds of the formula I according to the invention are notable for their strong inhibitory effect on the proliferation of cells, for example the proliferation of fibroblast cells and the proliferation of the smooth muscle cells of the blood vessels. For this reason, the compounds of the formula I are suitable for use as valuable therapeutic agents for disorders in which cell proliferation represents a primary or secondary cause, and can, therefore, be used as antiatherosclerotic agents, agents against late complications of diabetes, cancerous diseases, fibrotic diseases such as pulmonary fibrosis, hepatic fibrosis or renal fibrosis, and organ hypertrophies and hyperplasias, in particular hyperplasia or hypertrophy of the prostate.

The compounds according to the invention are efficient inhibitors of the cellular sodium/proton antiporter ($Na^+/H^+$ exchanger) which, in numerous diseases (essential hypertension, atherosclerosis, diabetes, etc.), is also elevated in cells which are readily accessible for measurement, such as, for example, erythrocytes, thrombocytes or leucocytes. The compounds according to the invention are therefore suitable for use as outstanding and simple scientific tools, for example in their use as diagnostic agents for determining and differentiating particular forms of hypertension and also of atherosclerosis, diabetes, proliferative diseases, etc. In addition to this, the compounds of the formula I are suitable for use in preventive therapy for preventing the genesis of high blood pressure, for example essential hypertension.

Pharmaceuticals which contain a compound I may, in this context, be administered orally, parenterally, intravenously, rectally or by inhalation, the preferred administration being dependent on the particular features of the disease. In this context, the compounds I can be used either alone or together with pharmaceutical auxiliary substances, and be used both in veterinary and in human medicine.

Owing to his specialist knowledge, the person skilled in the art is familiar with the auxiliary substances which are suitable for the desired pharmaceutical formulation.

In addition to solvents, gel formers, suppository bases, tablet auxiliary substances and other active compound excipients, antioxidants, dispersing agents, emulsifiers, defoamers, taste corrigents, preservatives, solubilizers or dyes can, for example, be used.

For an oral application form, the active compounds are mixed with the additives, such as excipients, stabilizers or inert diluents, which are suitable for this purpose, and brought by the customary methods into the suitable forms for administration, such as tablets, coated tablets, hard gelatin capsules or aqueous, alcoholic or oily solutions. Gum arabic, magnesium hydroxide, magnesium carbonate, potassium phosphate, lactose, glucose or starch, in particular corn starch, can, for example, be used as inert excipients. In this context, the preparation can be effected either as a dry granulate or a wet granulate. Vegetable or animal oils, for example, such as sunflower oil or cod liver oil, are suitable for use as oily excipients or as solvents.

For subcutaneous or intravenous administration, the active compounds, if desired together with the substances which are customary for this purpose, such as solubilizers, emulsifiers or further auxiliary substances, are brought into solution, suspension or emulsion. Examples of suitable solvents are: water, physiological sodium chloride solution or alcohols, for example ethanol, propanol or glycerol, and, in addition, sugar solutions such as glucose or mannitol solutions, or else a mixture of the different said solvents.

Examples of suitable pharmaceutical formulations for administration in the form of aerosols or sprays are solutions, suspensions or emulsions of the active compound of the formula I in a pharmaceutically harmless solvent, such as, in particular, ethanol or water, or in a mixture of such solvents.

As required, the formulation may also additionally contain other pharmaceutical auxiliary substances such as surfactants, emulsifiers and stabilizers and also a propellant gas. Such a preparation customarily contains the active compound in a concentration of from about 0.1 to 10, in particular of from about 0.3 to 3, % by weight. The dosage of the active compound of the formula I to be administered, and the frequency of administration, depend on the strength and the duration of the effect of the compounds used; they also depend on the nature and severity of the disease to be treated and also on the sex, age, weight and individual responsiveness of the mammalian subject to be treated.

On average, the daily dose of a compound of the formula I is, in the case of a patient of about 75 kg in weight, at least 0.001 mg/kg, preferably 0.01 mg/kg, up to at most 10 mg/kg, preferably 1 mg/kg, of body weight. In acute manifestations of the disease, for example immediately after suffering a cardiac infarction, still higher, and especially more frequent, dosages may be necessary, for example up to 4 individual doses per day. In the case of i.v. use, in particular, for example in the case of an infarction patient in intensive care, up to 200 mg per day may be necessary.

List of abbreviations:

| | |
|---|---|
| MeOH | methanol |
| DMF | N,N-dimethylformamide |
| EI | electron impact |
| DCI | desorption chemical ionization |
| RT | room temperature |
| EA | ethyl acetate (EtOAc) |
| mp | melting point |
| HEP | n-heptane |
| DME | dimethoxyethane |
| ES | electron spray |
| FAB | fast atom bombardment |
| $CH_2Cl_2$ | dichloromethane |
| THF | tetrahydrofuran |
| eq. | equivalent |
| Pd/C | palladium on carbon |
| Pt/C | platinum on carbon |
| LDA | lithium diisopropylamine |

Experimental section

General instructions for preparing acylguanidines (I) Variant A: from carboxylic acids (II, L=OH)

1.0 eq. of the carboxylic acid derivative of the formula II is dissolved or suspended in anhydrous THF (5 ml/mmol) and 1.1 eq. of carbonyldiimidazole are then added. After the reaction solution has been stirred at RT for 2 hours, 5.0 eq. of guanidine are introduced. After the mixture has been stirred overnight, the THF is distilled off under reduced pressure in a rotary evaporator; water is then added to the mixture which is adjusted with 2N HCl to between pH 6 and 7, after which the corresponding acylguanidine (formula I) is filtered off. The acylguanidines obtained in this way can be converted into the corresponding salts by being treated with aqueous, methanolic or ethereal hydrochloric acid or other pharmacologically tolerated acids.

General instructions for preparing acylguanidines (I) Variant B: from alkyl carboxylates (II, L=O-alkyl)

1.0 eq. of the alkyl carboxylate of the formula II and 5.0 eq. of guanidine (free base) are dissolved in isopropanol or suspended in THF and boiled under reflux (typical reaction time, from 2 to 5 h) until the reaction is complete (monitoring by thin layer chromatography). The solvent is distilled off under reduced pressure (in a rotary evaporator) and the residue is taken up in EA and washed 3× with $NaHCO_3$ solution. Drying takes place over $Na_2SO_4$ and the solvent is distilled off in vacuo; chromatography then takes place on silica gel using a suitable eluent, for example EA/MeOH 5:1. (Salt formation, compare variant A)

EXAMPLE 1

3-(3-Trifluoromethylphenyl)propionoguanidide

Hydrogenation of m-trifluoromethylcinnamic acid over 10% Pd/C in EA at RT and under standard pressure yielded 3-(3-trifluoromethylphenyl)propionic acid.

1.0 eq. of this saturated carboxylic acid was reacted with 1.1 eq. of carbonyldiimidazole and 5 eq. of guanidine in accordance with variant A. MS (ES):260 (M+1)

EXAMPLE 2

3-(2-Trifluoromethylphenyl)propionoguanidide

Hydrogenation of o-trifluoromethylcinnamic acid over 10% Pd/C in EA at RT and under standard pressure yielded 3-(2-trifluoromethylphenyl)propionic acid.

1.0 eq. of this saturated carboxylic acid was reacted with 1.1 eq. of carbonyldiimidazole and 5 eq. of guanidine in accordance with variant A. MS (ES):260 (M+1) mp: 73°–80° C.

EXAMPLE 3

3-(3-Trifluoromethoxyphenyl)propionoguanidide hydrochloride

Hydrogenation of m-trifluoromethoxycinnamic acid over 10% Pd/C in EtOH at RT and under standard pressure yielded 3-(3-trifluoromethoxyphenyl)propionic acid.

1.0 eq. of this saturated carboxylic acid was reacted with 1.1 eq. of carbonyldiimidazole and 5 eq. of guanidine in accordance with variant A and isolated as the hydrochloride. MS (ES):276 (M+1)

EXAMPLE 4

3-(4-Trifluoromethylphenyl)propionoguanidide

Hydrogenation of p-trifluoromethylcinnamic acid over 10% Pd/C in EA at RT and under standard pressure yielded 3-(4-trifluoromethylphenyl)propionic acid.

1.0 eq. of this saturated carboxylic acid was reacted with 1.1 eq. of carbonyldiimidazole and 5 eq. of guanidine in accordance with variant A. MS (ES):260 (M+1) mp:146°–153° C.

EXAMPLE 5

2-Methyl-3-(3-trifluoromethylphenyl)propionoguanidide hydrochloride

5a) Diethyl 2-methylmalonate was converted, in THF, into the anion using 1 eq. of sodium hydride and alkylated with 1.05 eq. of 3-trifluoromethylbenzyl bromide. After working up in the standard manner, diethyl 2-methyl-2-(3-trifluoromethylbenzyl)malonate was obtained. Colorless oil, MS (ES):333 (M+1)

5b) The diester from 4a) was hydrolyzed under reflux in glacial acetic acid/5N HCl and decarboxylated to give 2-methyl-3-(3-trifluoromethylphenyl)propionic acid. Colorless oil, MS (ES):233 (M+1)

5c) The carboxylic acid from 4b) was converted into the guanidide in accordance with variant A and isolated as the hydrochloride. Amorphous solid, MS (ES):274 (M+1)

EXAMPLE 6

2-Ethyl-3-(3-trifluoromethylphenyl)propionoguanidide

6a)

1 eq. of 3-(3-trifluoromethylphenyl)propionic acid was converted, in THF and at −78° C., into the dianion using 2 eq. of LDA (stirring for 30 min. at −78° C., then 30 min. at RT). 2 eq. of ethyl iodide were then added at −78° C. and the mixture was subsequently stirred at RT. Acidic working-up using 2N HCl and purification by chromatography yielded 2-ethyl-3-(3-trifluoromethylphenyl)-propionic acid.

6b) The carboxylic acid from 6a) was converted into the guanidide in accordance with variant A and isolated as the free base. Colorless oil, MS (ES):288 (M+1)

EXAMPLE 7

2-Isopropyl-3-(3-trifluoromethylphenyl)propionoguanidide Was prepared in analogy with Example 6. Colorless oil, MS (ES):302 (M+1)

EXAMPLE 8

2-Isobutyl-3-(3-trifluoromethylphenyl)propionoguanidide Was prepared in analogy with Example 6. Amorphous solid, MS (ES):316 (M+1)

EXAMPLE 9

2-Ethyl-3-[3,5-bis(trifluoromethyl)phenyl]-propionoguanidide Was prepared in analogy with Example 5. Colorless oil, MS (ES):356 (M+1)

EXAMPLE 10

2-(2-Trifluoromethylphenyl)acetoguanidide hydrochloride Was obtained from the corresponding acetic acid derivative in accordance with variant A. MS (ES):246 (M+1) mp:135°–141° C.

EXAMPLE 11

2-(3-Trifluoromethylphenyl)acetoguanidide hydrochloride Was obtained from the corresponding acetic acid derivative in accordance with variant A. MS (ES):246 (M+1) mp: 122°–126° C.

EXAMPLE 12

2-(4-Trifluoromethylphenyl)acetoguanidide hydrochloride Was obtained from the corresponding acetic acid derivative in accordance with variant A. MS (ES):246 (M+1) mp: 102°–107° C.

Pharmacological data:

Inhibition of the $Na^+/H^+$ exchanger of rabbit erythrocytes:

New Zealand White rabbits (Ivanovas) were given a standard diet containing 2% cholesterol for 6 weeks in order to activate $Na^+/H^+$ exchange and thus render it possible to determine the $Na^+$ influx into the erythrocytes via $Na^+/H^+$ exchange by flame photometry. The blood was removed from the aural arteries and rendered incoagulable using 25 IU/ml potassium heparin. A portion of each sample was used for determining, in duplicate, the hematocrit by centrifugation. Aliquots of in each case 100 μl were used for measuring the initial content of $Na^+$ in the erythrocytes.

In order to determine the amiloride-sensitive sodium influx, 100 μl of each blood sample were incubated, at pH 7.4 and 37° C., in in each case 5 ml of a hyperosmolar salt/sucrose medium (mmol/l:140 NaCl, 3 KCl, 150 sucrose, 0.1 ouabain, 20 tris(hydroxymethyl)aminomethane). After that, the erythrocytes were washed three times with ice-cold $MgCl_2$/ouabain solution (mmol/l: 112 $MgCl_2$, 0.1 ouabain), and haemolyzed in 2.0 ml of distilled water. The intracellular content of sodium was determined by flame photometry.

The net influx of $Na^+$ was calculated from the difference between the initial sodium values and the sodium content of the erythrocytes after incubation. The amiloride-inhibitable sodium influx was given by the difference in the sodium content of the erythrocytes after incubation with and without $3 \times 10^{-4}$ mol/l amiloride. The same procedure was employed for the compounds according to the invention.

$Na^+/H^+$-exchanger inhibition results:

| Example | IC $_{50}$ (µmol) |
|---------|-------------------|
| 1 | 0.6 |
| 2 | 0.5 |
| 3 | 0.7 |
| 5 | 0.05 |

We claim:

1. A phenyl-substituted alkylcarboguanidide, carrying at least one perfluoroalkyl group, of the formula I

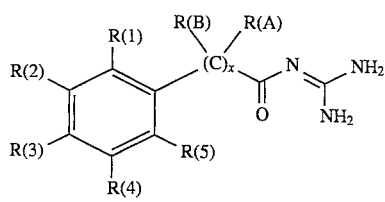

in which:

R(A) is hydrogen, F, Cl, Br, I, CN, OR(6), $(C_1-C_4)$-alkyl, $-C_bF_{2b+1}$ or NR(7)R(8);

b is 1, 2, 3, or 4;

R(6) is hydrogen, $(C_1-C_4)$-alkyl, $(C_1-C_4)$-perfluoroalkyl, phenyl or benzyl, where the aromatic radicals are unsubstituted or substituted by 1–3 substituents selected from the group consisting of F, Cl, $CF_3$, methyl, methoxy and NR(9)(10), R(9) and R(10) are H, $CH_3$ or $CF_3$;

R(7) and R(8) are, independently of each other, defined as R(6);

R(B) is, independently, defined as R(A);

X is 2;

R(1) is hydrogen, $(C_1-C_4)$-alkyl, $-C_eF_{2e+1}$, F, or Cl;

e is 1, 2, 3, or 4;

R(2), R(3), R(4) end R(5) are, independently of each other, defined as R(1), with the condition, however, that at least one of the substituents R(1), R(2), R(3), R(4), R(5), R(A) and R(B) is a $-C_eF_{2e+1}$ or a $-C_bF_{2b+1}$ group, or a pharmaceutically tolerated salt thereof.

2. A pharmaceutical composition for treating (1) cardiac infarct, (2) angina pectoris, (3) arrhythmia, (4) a disease caused by ischemic conditions, (5) a shock condition, or (6) a disease in which cell proliferation is a primary or secondary cause; for inhibiting the Na+/H+ exchanger; for diagnosing hypertension, atherosclerosis, diabetes or a proliferative disease; for use in a surgical operation or organ transplant; or for use in preserving and storing a transplant for surgical procedure, which comprises an effective amount of a compound of formula I or a salt thereof as claimed in claim 1 together with a pharmaceutically acceptable carrier.

3. A method of treating or preventing a disease caused by ischemic conditions, which comprises administering to a host in need of said treatment an effective amount of a compound of formula I or a salt thereof as claimed in claim 1.

* * * * *

UNITED STATES PATENT AND TRADEMARK OFFICE
CERTIFICATE OF CORRECTION

PATENT NO. : 5,567,734
DATED : October 22, 1996
INVENTOR(S) : Jan-Robert SCHWARK et al.

It is certified that error appears in the above-indentified patent and that said Letters Patent is hereby corrected as shown below: Title page, item [54] and col. 1, In the Title, line 5, before "DIAGNOSTIC" delete "A"

Title page, item [57],
In the Abstract, line 8, "-$O_{0-1}$ ($CH_2$) $O_{0-1}$ perfluoroalkyl" should read ---$O_{0-1}$ ($CH_2$)$_{0-1}$ perfluoroalkyl--.

Claim 1, column 10, line 11, "end" should read --and--.

Signed and Sealed this

Twenty-eighth Day of January, 1997

Attest:

BRUCE LEHMAN

Attesting Officer    Commissioner of Patents and Trademarks